United States Patent
Peterson et al.

(10) Patent No.: US 6,308,714 B1
(45) Date of Patent: *Oct. 30, 2001

(54) ULTRASOUND ENHANCED CHEMOTHERAPY

(75) Inventors: Thomas M. Peterson, Erie, PA (US); Robert J. Siegel, Venice, CA (US)

(73) Assignee: Coraje, Inc., San Francisco, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/189,608

(22) Filed: Nov. 10, 1998

(51) Int. Cl.7 ...................................................... A61B 19/00
(52) U.S. Cl. ................................ 128/898; 604/19; 604/22
(58) Field of Search ............................... 128/898; 604/19, 604/22; 601/2

(56) References Cited

U.S. PATENT DOCUMENTS

| | | | |
|---|---|---|---|
| 4,841,045 | * | 6/1989 | Kuehne ................................ 540/478 |
| 4,897,477 | * | 1/1990 | Kuehne ................................ 540/478 |
| 4,989,601 | | 2/1991 | Marchosky ........................... 128/399 |
| 5,158,536 | | 10/1992 | Sekins ..................................... 604/20 |
| 5,403,575 | | 4/1995 | Kaufman .............................. 424/1.89 |
| 5,490,840 | * | 2/1996 | Uzgiris et al. .......................... 604/22 |
| 5,562,608 | | 10/1996 | Sekins ..................................... 604/20 |
| 5,567,765 | | 10/1996 | Moore .................................. 524/801 |
| 5,679,394 | | 10/1997 | Long, Jr. .............................. 424/450 |
| 5,707,352 | | 1/1998 | Sekins .................................... 604/56 |
| 5,947,921 | * | 9/1999 | Johnson et al. ........................ 604/22 |
| 5,984,882 | * | 11/1999 | Rosenchein et al. ..................... 601/2 |
| 6,002,961 | * | 12/1999 | Mitragotri et al. ..................... 604/20 |
| 6,028,066 | * | 2/2000 | Unger ................................... 514/180 |
| 6,113,558 | * | 9/2000 | Rosenchein et al. ..................... 601/2 |
| 6,135,976 | * | 10/2000 | Tachibana et al. ...................... 604/21 |

* cited by examiner

Primary Examiner—Dinh X. Nguyen
(74) Attorney, Agent, or Firm—Walter A. Hackler

(57) ABSTRACT

Apparatus and method is provided for enhancing the action of anti-cancer agents, which includes the introduction of anti-cancer agent into or proximate a tumor within a body and thereafter introducing ultrasonic energy at the solid tumor with the introduced anti-cancer agent. The ultrasonic energy is sufficient to increase the anti-cancer activity on the solid tumor without significant heating of the solid tumor or surrounding tissue.

28 Claims, 1 Drawing Sheet

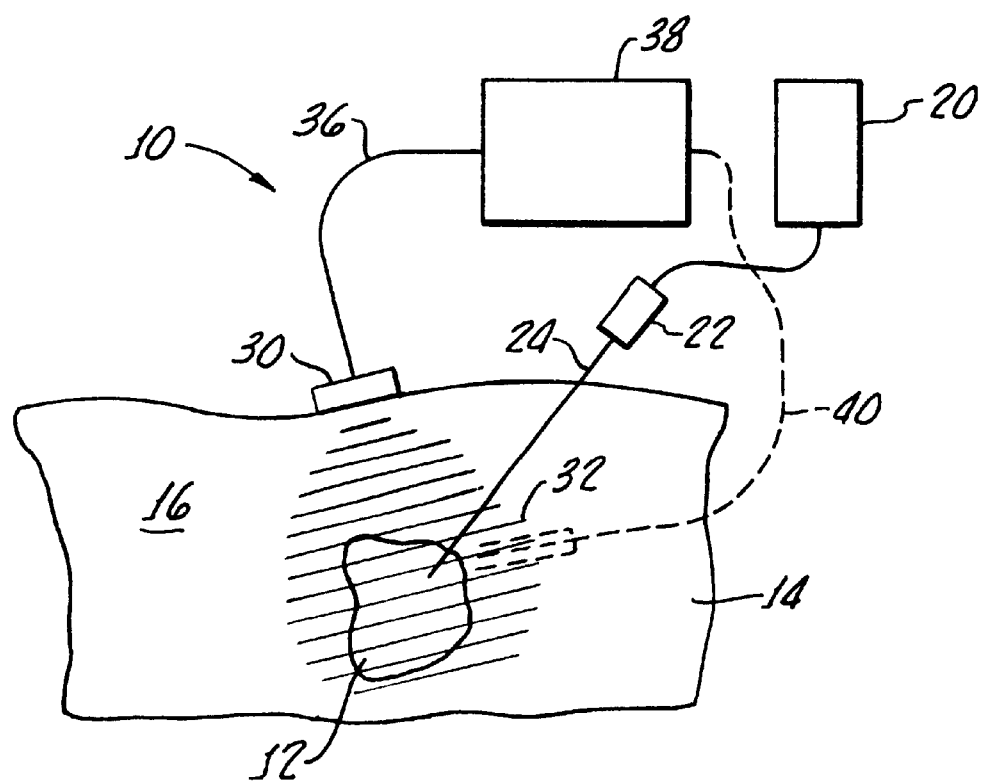

ULTRASOUND ENHANCED CHEMOTHERAPY

The present invention relates to apparatus and methods for the delivery of active agents using ultrasonic energy.

It is well known that the clinical utility of many pharmaceutics is limited by drug delivery. That is, a great number of agents showing promising biological activity are not utilized because of problems of undesirable toxicity, bioavailability, solubility, and a requirement of local sustained drug concentration among others.

The present invention is directed to administration of anti-cancer agents which improves or enhances the activity of such agents or drugs.

Cancer results from an abnormal, rapid growth of cells which divide and multiply. Such cells may become tumors that invade healthy tissue. Many anti-cancer agents have been developed which work along different biological pathways in order to reduce or eliminate cancer cell growth; however, the human pharmacokinetics may make the agents difficult to deliver.

The present invention is not directed to any drug formulation or composition but rather to apparatus and method for delivering such drugs or agents.

Modalities for the treatment of malignant growths generally include surgery, radiation therapy and chemotherapy. Surgery, while often effective for solid tumors, is in many instances difficult to perform and a total removal of cancerous cell is often not obtainable.

Accordingly, in combination with surgery, or as a separate modality of treatment, radiation therapy and chemotherapy have been utilized. Radiation therapy has a disadvantage of killing healthy tissue as well as cancerous tissues in exposed areas, and chemotherapy also may result in damage to the surrounding normal tissue. This factor is particularly important in many anti-cancer drugs, such as anthracycline antibiotics such as adriamycin and daunorubricin. The beneficial facts of these drugs relate to their nucleotide base intercalation and cell membrane lipid binding activities. This particular class of drugs has dose limiting toxicities due to myelo suppression.

Ultrasound at high energy can generate heat within tissue and accordingly has been used in hyperthermic treatment of cancerous tumors. For example, hyperthermia induces doxorubicin release from long-circulating liposomes and enhances their anti-tumor efficacy.

The present invention utilizes low energy ultrasound and local drug delivery to enhance the effectiveness of anti-cancer drugs and or treatment. Such enhancement is beneficial in reducing the effective dose of the drugs necessary for sufficient anti-cancer activity. Such reduced dose levels translate into reducing unwanted toxicity of the anti-cancer agents.

SUMMARY OF THE INVENTION

A method of anti-cancer drug delivery in accordance with the present invention generally comprises introducing an anti-cancer agent into a solid tumor within a body, and thereafter introducing ultrasonic energy into the solid tumor with sufficient energy to increase the anti-cancer activity on the solid tumor, without significant heating of the solid tumor in surrounding tissue.

This enhanced activity is not caused by overall heating of the tumor and tissue with ultrasound in view of the fact that the ultrasound energy is at relatively low frequency and low power.

The ultrasonic energy may be generated external to the body and has an energy of less than 50 watts at an operating frequency of less than about 100 Kz. The ultrasonic energy may alternatively be introduced by a catheter.

More particularly, the method in accordance with the present invention may utilize an anti-cancer drug selected from the group consisting of alkylating agents, agents with alkylator activity, antimetabolites, antitumor antibiotics, plant alkaloids, enzymes, hormonal agents and anti-angiogenesis agents.

Still more particularly, the present invention may utilize an anti-cancer agent selected from the group consisting of: Adriamycin, Alkeran, AntiVEGF monoclonal antibody SU5416, Aredia, Arimidex, BiCNU, Bleomycin, Blenoxane, Camptosar, Casodex, CeeNU, Celestone, CM101, Soluspan Suspension, CA1, Cerubidine, Cisplatin, Cosmegen, Cytosar U, Cytoxan, Daunorubricin, DaunoXome, Depo-Provera Sterile Aqueous Suspension, Didronel, Diethylstilbestrol, Diflucan, Doxil, Doxorubicin Hydrochloride, DTIC-Dome, Elspar, Emcyt, Epogen, Ergamisol Ethyol, Etopophos, Etoposide, Eulexin, Femara, Fludara, Fluorouracil, Gemzar, Gliade, Hexalen, Hycamtin, Hydrea, Hydroxyurea, Idamycin, Iflex, Intron A, Kytril, Leucovorin Calcium, Leukeran, Leukine, Leustatin, Lupron, Lysodren, Marinol, Matulane, Mesnex, Methotrexate Sodium, Mithracin, Mitoxantrosc, Mustargen, Mutamycin, Myleran, Navelbine, Neupogen, Nilandron, Nipent, Nolvadex, Novantrone, Oncaspar, Oncovin, Paraplatin, Photofrin, Platinol, Procrit, Proleukin, Purinethol, Roferon A, Rubex, Salagen, Sandostatin, Squalamine, Sterile FUDR, Taxol, Taxotere, Teslac, Thalidomide, Thera-Cys BCG, Thioguanine, Thioplex, Tice BCG, TNP 470, Velban, Vesanoid, VePesid, Vitaxin, Vumon, Zanosar, Zinecard, Zofran, Zoladex, Zyloprim and 2-methoxy-oestradiol.

The method of the present invention includes introducing an anti-cancer drug proximate cancer cells and promoting intracellular activation by irradiating the cancer cells with ultrasound to cause passage of the anti-cancer drug into the cancer cells.

More particularly, the anti-cancer drug may be an anti-angiogenesis agent.

The apparatus in accordance with the present invention for conducting the method generally includes a means for introducing an anti-cancer agent into a solid tumor within the body and ultrasonic means for radiating solid tumors with sufficient energy to increase the anti-cancer activity of the agent on the solid tumor without significant heating of the solid tumor, or surrounding tissue, by the radiated ultrasound. As part of the present invention, the means for introducing the anti-cancer agent may include microbubbles. In this embodiment, one or more of the hereinabove referenced active agents is incorporated into microbubbles introduced into a tumor. In conforming to the preferred method of the present invention, the preferred apparatus includes an ultrasonic generator for radiating the solid tumor, which is disposed outside of the body.

BRIEF DESCRIPTION OF THE DRAWINGS

The present invention may be better understood with reference to the following detailed description, taken in conjunction with the accompanying drawing, in which FIG. 1 is a representation of a method and apparatus in accordance with the present invention.

DETAILED DESCRIPTION OF THE DRAWINGS

While it is well known that elevating a temperature of various chemotherapeutic drugs only a few degrees may increase the effective level of the drug, a major problem is the deliverance of such anti-cancer drugs while maintaining the temperature thereof within a solid tumor at a controlled elevated temperature for any extended period of time. That is, Ultrasound has been used heretofore for the heating of body tissue; however, raising the temperature of an anti-cancer drug within a solid tumor to a desired level presents significant problems.

The present invention, however, is not directed to nor incorporates the principle of heat elevation for increased activity. Rather, a low energy ultrasound is utilized in combination with an anti-cancer drug to provide a synergistic and beneficial enhancement of drug activity without heating or the requirement for a controlled temperature elevation.

With reference to FIG. 1, there is represented apparatus 10 in accordance with the present invention for treating of a solid tumor, or the like, 12, disposed within a body 14 comprising surrounding tissue 16. The apparatus 10 is suitable for practicing the method of the present invention, which provides for the enhancement of the action of an anti-cancer agent in the treatment of the solid tumor 12. Suitable apparatus for generating external ultrasound for transdermal delivery is taught in U.S. Pat. No. 5,509,896. This patent is to be incorporated herewith in its entirety for the purpose of describing such equipment.

Again, with reference to FIG. 1, the apparatus 10 in accordance with the present invention may include a vial 20 for an anti-cancer agent which, by way of a valve 22 and a catheter 24, provides a means for injecting, introducing and delivering the agents into the solid tumor 12, or, proximate the solid tumor 12 in the surrounding tissue 16 within the body 14.

Alternatively, the anti-cancer agents may be introduced or injected into the solid tumor 12 by any conventional manner, including, for example, intravenously, interarterial or directly into the tumor 12.

It should be appreciated that the anti-cancer drugs may be introduced directly, as hereinabove noted, or incorporated within microbubbles or along with microbubbles. It is expected that further enhancement of drug activity occurs with the use of microbubbles.

With regard to suitable microbubbles, reference is made to echo contrast agents commonly utilized for diagnostic. Accordingly, suitable microbubbles in accordance with the present invention include: free gas bubbles, stabilized gas bubbles, colloidal suspensions, emulsions, and aqueous solutions. The aqueous solutions include aqueous solutions of air-filled proteinaceous microbubbles. Currently available products include gas filled liposomes, gas filled lipid bilayers, microbubbles containing liquids, gas emulsions, gas-filled microspheres and microbubbles containing suspensions.

Incorporation of the anti-cancer agents into the microbubbles may be made in any conventional manner.

A conventional transducer 30 coupled to the body 14 in any suitable manner provides a means for introducing ultrasonic energy into the solid tumor 12 with sufficient energy to increase the anti-cancer activity of the agent on the solid tumor without significant heating of the solid tumor 12, or surrounding tissue 16, the radiation being represented by a plurality of lines 32, shown in FIG. 1.

The transducer 30 is connected via a line 36 to an ultrasonic generator 38, which is preferably disposed exterior to the body 14.

Alternatively, an ultrasonic probe 40, shown in dashed line, may be inserted into the body 14 proximate, or into, the solid tumor 12, for the deliverance of ultrasonic energy thereinto.

The ultrasonic generator 38 may be of conventional design as hereinabove noted, and have a power output of up to, for example, about 50 watts, as measured from the transducer 30. Importantly, the power levels provided by the generator 38 and transducer 30 are less than that required to significantly heat the solid tumor 12, or surrounding tissue 16, within the body 14.

As hereinabove noted, ultrasound may be transmitted intravascularly, rather than transcutaneously, and in that regard, a miniature ultrasonic transducer (not shown) such as the device described in U.S. Pat. No. 5,269,291, may be utilized as a means for transmitting ultrasonic energy directly into proximate the solid tumor 12 and surrounding tissue 16. This U.S. Pat. No. 5,269,291 is incorporated in toto herein by this specific reference thereto for providing an example of a suitable intravascular ultrasound transducer.

Ultrasound enhancement provided by the apparatus and method of the present invention is most crucial when the anti-cancer drug being administered is very toxic. Specific examples of such drugs are the anthracycline antibiotics such as adriamycin and daunorubricin. The beneficial effects of these drugs relate to their nucleotide base intercalation and cell membrane lipid binding activities. This class of drugs has dose limiting toxicities due to myelo suppression, i.e., bone marrow suppression, and cardiotoxicity.

However, other drugs considered to be within the scope of the present invention include: Adriamycin PFS Injection (Pharmacia & Upjohn); Adriamycin RDF for Injection (Pharmacia & Upjohn); Alkeran for Injection (Glaxo Wellcome Oncology/HIV); Aredia for Injection (Novartis); BiCNU (Bristol-Myers Squibb Oncology/Immunology); Blenoxane (Bristol-Myers Squibb Oncology/Immunology); Camptosar Injection (Pharmacia & Upjohn); Celestone Soluspan Suspension (Schering); Cerubidine for Injection (Bedford); Cosmegen for Injection (Merck); Cytoxan for Injection (Bristol-Myers Squibb Oncology/Immunology); DaunoXome (NeXstar); Depo-Provera Sterile Aqueous Suspension (Pharmacia & Upjohn); Didronel I.V. Infusion (MGI); Doxil Injection (Sequus); Doxorubicin Hydrochloride for Injection, USP (Astra); Doxorubicin Hydrochloride Injection, USP (ASTRA); DTIC-Dome (Bayer); Elspar (Merck); Epogen for Injection (Amgen); Ethyol for Injection (Alza); Etopophos for Injection (Bristol-Myers Squibb Oncology/Immunology); Etoposide Injection (Astra); Fludara for Injection (Berlex); Fluorouracil Injection (Roche Laboratories); Gemzar for Injection (Lilly); Hycamtin for Injection (SmithKline Beecham); Idamycin for Injection (Pharmacia & Upjohn); Ifex for Injection (Bristol-Myers Squibb Oncology/Immunology); Intron A for Injection (Schering); Kytril Injection (SmithKline Beecham); Leucovorin Calcium for Injection (Immunex); Leucovorin Calcium for Injection, Wellcovorin Brand (Glaxo Welcome Oncology/HIV); Leukine (Immunex); Leustatin Injection (Ortho Biotech); Lupron Injection (Tap); Mesnex Injection (Bristol-Myers Squibb Oncology/Immunology); Methotrexate Sodium Tablets, Injection, for Injection and LPF Injection (Immunex); Mithracin for Intravenous Use (Bayer); Mustargen for Injection (Bristol-Myers Squibb Oncology/Immunology); Mutamycin for Injection (Bristol-Myers Squibb Oncology/Immunology); Navelbine Injection (Glaxo Wellcome Oncology/HIV); Neupogen for Injection (Amgen); Nipent for Injection (SuperGen); Novantrone for Injection (Immunex); Oncaspar (Rhone-Poulenc Rorer); Oncovin Solution Vials & Hyporets (Lilly); Paraplatin for Injection (Bristol-Myers Squibb Oncology/Immunology); Photofrin for Injection (Sanofi); Platinol for Injection (Bristol-Myers Squibb Oncology/Immunology); Platinol- AQ Injection (Bristol-Myers Squibb Oncology/ Immunology); Procrit for Injection (Ortho Biotech); Proleukin for Injection (Chiron Therapeutics); Roferon-A Injection (Roche Laboratories); Rubex for Injection (Bristol-Myers Squibb Oncology/Immunology); Sandostatin Injection (Novartis); Sterile FUDR (Roche Laboratories); Taxol Injection (Bristol-Myers Squibb Oncology/Immunology); Taxotere for Injection Concentrate (Rhone-Poulenc Rorer); TheraCys BCG Live (Intravesical) (Pasteur Merieux Connaught); Thioplex for Injection (Immunex); Tice BCG Vaccine, USP (Organon); Velban Vials (Lilly); Vumon for Injection (Bristol-Myers Squibb Oncology/Immunology); Zinecard for Injection (Pharmacia & Upjohn); Zofran Injection (Glaxo Wellcome Oncology/HIV); Zofran Injection Premixed (Glaxo Wellcome Oncology/HIV); Zoladex (Zeneca).

Other classes of drugs considered to be within the scope of the present invention include alkylating agents which target DNA and are cytoxic, nutagenic, and carcinogenic. All alkylating agents produce alkylation through the formation of intermediate. Alkylating agents impair cell function by transferring alkyl groups to amino, cartoryl, sulfhydryl, or phosphate groups of biologically important molecules.

Tumor resistance to these drugs appears to be related to the capacity of cells to repair nucleic acid damage and to inactivate the drugs by conjugation with glutathione. Ultrasound is introduced to reduce such tumor resistance. In particular, such drugs include Busulfan (Myleran), Chlorambucil (Leukeran), Cyclophosphamide (Cytoxan, Neosor, Endoxus), Ifosfamide (Isophosphamide, Ifex), Melphhalan (Alkeran, Phenylalanine Mustargen, L-Pam, L-Sarcolysin), Nitrogen Mustargen (Mechlorethamine, Mustargen, $HIV_2$), Nitrosonceas (Carmustine CBCNV, Bischlorethyl, Nitrosourea), Lomustine (CCNV, Cyclohexyl Chlorethyl Nitrosouren, CeeNV), semustine (methyl-CCNV) and Streptozocin (Strephozotocin), Streptozocin (Streptozoticin, Zanosan), Thiotepa (Theo-TEPA, and Triethylenethrophosphoranide).

Other agents with alkylator activity include a group of compounds which comprise heavy metal alkylators (platinum complexes) that act predominantly by covalent bonding and "non-classic alkylating agents". Such agents typically contain a Chloromethyl groups and an important N-methyl group. Such other agents include Amsacrine (m-AMSA, msa, Acridinylanisidiale, 4'-)(9-acridinylamins) methanesulfin-m-anesidide, Carboplatin (Paraplatin, Carboplatinum, CBDCA), Cisplatin (Cesplatinum), Dacabazine (DTIC, DIC dimethyltricizenormidazoleconboxamide), Hexamethylmelanine (HMM, Altretanine, Hexalin) and Procarbazine (Matulane, Natulanan).

Antimelabolites have pharmacokinetics characterized by non-linear dose response curves. That is, after a certain dose, no more cells are killed with increasing doses. Ultrasound is used to increase the effectiveness of the drugs at low level doses. Such drugs include Azacitidine (5-azacylidine, ladakamycin) Cladribine (2-CdA, CdA, 2-chloro-2-deoxyadenosine) Cytarabine (Cytosine Arabinoside, Cytosar, Tarabine), Fludarabine (2-fluoroadenine arabinoside-5-phosphate, fludara). Fluorouracil (5-FV, Adrucil, Efuctex) Hydroxyurea (hydroxycarbamide, Hydrea), Leucovorin (Leucovorin Calcium), Mercaptopurine (G-MP, Purinethol), Methotrexate (Amethopterin), Mitoguazone(Methyl-GAG), Pentostatin (2'-deorycoformycin) and Thioguanine (6-TG, aminopurine-6-thiol-hemihydrate).

Antitumor antibiotics generally are drugs derived from microorganisms. Many of these drugs interfere with DNA through intercalation, a reaction whereby the drug inserts itself between DNA base pairs. Introduction of ultrasound enhances this interference. Such drugs include Actinomycin DC Cosmegen, Dactinomycin), Bleomycin (Blenoxane) Daunoxubibin (rubidomycin), Doxorubicin (Adriamycin, Hydroxydaunorubicin, hydroxydaunomycin, Rubex).

Because of the toxicity of Adriamycin, local dosing is required and is enabled with ultrasound. The drug is slowly pushed through a running line IV line over 2–5 minutes using intravasation precautions or continuously infused through a central venous line while introducing ultrasound; Idarubicin (44-demethylorydan norubicin, Idamycin), Mithramycin (Mithracin, Plicamycin), Milomycin C and Mitorantione (Novantrone).

Plants alkaloids bind to microtubular proteins thus inhibiting microtubule assembly. Ultrasound is introduced to increase such binding. Such alkaloids include Etoposide, Paclitaxel (Taxol), Treniposide, Vinblastine (Velban, Velsar, Alkaban), Vincristine (Oncovin, Vincasar, Leurocristine) and Vindesine (Eldisine).

Hormonal agents include Adrenocorticosteroids, Adrenocorticosteroid inhibitors, Mitolane, Androzens, Antiandiozens, Antiestrogens, Estrogens, LHRH agonists, Progesterones.

Antiangiogenesis agents hereinabove discussed include Fumagillin-derivative TNP-470, Platelet Factor 4, Interleukin-12, Metalloproteinase inhibitor Batimastat, Carboryaminatriarzole, Thalidomide, Interferon Alfa-2a, Linomide and Sulfated Polysaccharide Tecogalan (DS-4152).

While not being bound by a precise mechanism, it is believed that the introduction of ultrasound enhances the permeability of an active agent thus enabling more of the agent to be taken up by the cells which increases the efficacy of the agent. This is a form of vasodilation. In other words, ultrasound causes a sonoporation of the cells which in effect alters the cellular membrane to effect greater drug or agent absorption.

EXAMPLE I

A patient with hepatic metastases is treated by direct perfusion of fluorouracil, flexuridine or Adriamycin anti-cancer drug, and solid tumor therein, into the liver through hepatic artery cannulation while introducing ultrasound energy at less than 100 kHz and less than 50 W. Up to less than 80% anti-cancer drug is utilized in combination with ultrasound, (as is compared to treatment without ultrasound), less drug toxicity is experienced.

EXAMPLE II

The procedure set forth in Example I is repeated with the anti-cancer drug when it is administered with microbubbles and still less drug toxicity is experienced.

EXAMPLE III

A patient having peritoneal carcinomatosis with malignant carcinematosis is treated by instillation of chemotherapy directly into the abdomen to control malignant effusions while introducing ultrasound at less than 100 kHz and less than 50 W. The abdomen is drained to be as dry as possible, preferably using a peritoneal dialysis catheter. The chosen drug is dissolved in 100 ml of normal saline, injected into the catheter and followed by another 100 ml of normal saline for flushing. The patient's position is shifted every few minutes for an hour to disperse the drug. The use of ultrasound increases the interval of repeated doses. The chosen drug is bleomycin (15 units), 5-fluorouracil (1000 mg), thiotepa (45 mg) Adriamycin (30 mg) cisplatin, or a-IFN.

EXAMPLE IV

The procedure set forth in Example III is repeated with the chosen drug administered with microbubbles and the interval of repeated doses is further increased.

EXAMPLE V

The procedures set forth in Examples I–IV are repeated using ultrasound at an energy level up to 1 mHz with power levels to 150 watts with decreasing effectiveness.

Although there has been hereinabove described a specific arrangement of ultrasonic apparatus and a method for the enhancement of action of anti-cancer agents, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. A method of anti-cancer drug delivery comprising the steps of:
   introducing an anti-cancer drug into a solid tumor within a body; and
   transcutaneous introducing ultrasonic energy into the solid tumor while the anti-cancer drug is present therein, the ultrasonic energy being less than about 100 kHz at less than about 50 watts in order to prevent heating of the tumor.

2. The method according to claim 1 wherein the ultrasonic energy is introduced by a catheter.

3. The method according to claim 1 wherein the ultrasonic energy is introduced transcutaneously.

4. The method according to claim 1 wherein the ultrasonic energy is introduced with sufficient energy and frequency to cause vasodilation within the tumor.

5. The method according to claim 1 wherein the anti-cancer drug is selected from the group consisting of alkylating agents, agents with alkylator activity, antimelabolites, anti-tumor antibiotics, plant alkaloids, enzymes, hormonal agents and anti-angiogenesis agents.

6. The method according to claim 1 wherein said anti-cancer agent is selected from the group consisting of: Adriamycin, Alkeran, AntiVEGF monoclonal antibody SU5416, Aredia, Arimidex, BiCNU, Bleomycin, Blenoxane, Camptosar, Casodex, CeeNU, Celestone, CM101 Soluspan Suspension, CA1, Cerubidine, Cisplatin, Cosmegan, Cytosar U, Cytoxan, Daunorubricin, DaunoXome, Depo-Provera Sterile Aqueous Suspension, Didronel, Diethylstilbestrol, Diflucan, Doxil, Doxorubicin Hydrochloride, DTIC-Dome, Elspar, Emcyt, Epogen, Ergamisol, Ethyol, Etopophos, Etoposide, Eulexin, Femara, Fludara, Fluorouracil, Gemzar, Gliade, Hexalen, Hycamtin, Hydrea, Hydroxyurea, Idamycin, Iflex, Intron A, Kytril, Leucovorin Calcium, Leukeran, Leukine, Leustatin, Lupron, Lysodren, Marinol, Matulane, Mesnex, Methotrexate Sodium, Mithracin, Mitoxantrosc, Mustargen, Mutamycin, Myleran, Navelbine, Neupogen, Nilandron, Nipent, Nolvadex, Novantrone, Oncaspar, Oncovin, Paraplatin, Photofrin, Platinol, Procrit, Proleukin, Purinethol, Roferon A, Rubex, Salagen, Sandostatin, Squalamine, Sterile FUDR, Taxol, Taxotere, Teslac, Thalidomide, TheraCys BCG, Thioguanine, Thioplex, Tice BCG, TNP 470, Velban, Vesanoid, VePesid, Vitaxin, Vumon, Zanosar, Zinecard, Zofran, Zoladex, Zyloprim, 2 Methoxy-oestradiol.

7. The method according to claim 1 wherein the step of introducing an anti-cancer drug includes incorporating the anti-cancer drug into microbubbles before introduction into the tumor.

8. The method according to claim 1 further comprising the step of introducing microbubbles into the tumor with the anti-cancer drug.

9. A method of anti-cancer drug delivery comprising the steps of:
   introducing an anti-cancer drug proximate cancer cells; and
   promoting intracellular activation by irradiating the cancer cells with ultrasound to cause passage of the anti-cancer drug into the cancer cells, the ultrasound having the energy of less than about 50 watts and a frequency of less than 100 kHz in order to prevent heating of the cancer cell.

10. The method according to claim 9 wherein the ultrasonic energy is introduced by a catheter.

11. The method according to claim 9 wherein the ultrasonic energy is introduced transcutaneously.

12. The method according to claim 9 wherein the step of introducing an anti-cancer drug includes incorporating the anti-cancer drug into microbubbles before introduction proximate cancer cells.

13. The method according to claim 9 further comprising the step of introducing microbubbles proximate the cancer cells with the anti-cancer drug.

14. A method for enhancing the action of an anti-cancer agent in the treatment of a solid tumor, said method comprising the steps of:
   introducing an anti-cancer agent into a solid tumor within a body; and
   introducing ultrasonic energy into the solid tumor, said ultrasonic energy being of sufficient energy to increase the anti-cancer activity of the agent on the solid tumor without significant heating of the solid tumor or surrounding tissue, said ultrasonic energy being less than about 100 kHz at less than about 50 watts in order to prevent heating of the tumor.

15. The method according to claim 14 wherein the ultrasonic energy is introduced by a catheter.

16. The method according to claim 14 wherein the ultrasonic energy is introduced transcutaneously.

17. The method according to claim 14 wherein the ultrasonic energy is introduced with sufficient energy and frequency to cause vasodilation within the tumor.

18. The method according to claim 14 wherein the anti-cancer drug is selected from the group consisting of alkylating agents, agents with alkylator activity, antimelabolites, anti-tumor antibiotics, plant alkaloids, enzymes, hormonal agents and anti-angiogenesis agents.

19. The method according to claim 14 wherein said anti-cancer agent is selected from the group consisting of: Adriamycin, Alkeran, AntiVEGF monoclonal antibody SU5416, Aredia, Arimidex, BiCNU, Bleomycin, Blenoxane, Camptosar, Casodex, CeeNU, Celestone, CM101 Soluspan Suspension, CA1, Cerubidine, Cisplatin, Cosmegan, Cytosar U, Cytoxan, Daunorubricin, DaunoXome, Depo-Provera Sterile Aqueous Suspension, Didronel, Diethylstilbestrol, Diflucan, Doxil, Doxorubicin Hydrochloride, DTIC-Dome, Elspar, Emcyt, Epogen, Ergamisol, Ethyol, Etopophos, Etoposide, Eulexin, Femara, Fludara, Fluorouracil, Gemzar, Gliade, Hexalen, Hycamtin, Hydrea, Hydroxyurea, Idamycin, Iflex, Intron A, Kytril, Leucovorin Calcium, Leukeran, Leukine, Leustatin, Lupron, Lysodren, Marinol, Matulane, Mesnex, Methotrexate Sodium, Mithracin, Mitoxantrosc, Mustargen, Mutamycin, Myleran, Navelbine, Neupogen, Nilandron, Nipent, Nolvadex, Novantrone, Oncaspar, Oncovin, Paraplatin, Photofrin, Platinol, Procrit, Proleukin, Purinethol, Roferon A, Rubex, Salagen, Sandostatin, Squalamine, Sterile FUDR, Taxol, Taxotere, Teslac, Thalidomide, TheraCys BCG, Thioguanine, Thioplex, Tice BCG, TNP 470, Velban, Vesanoid, VePesid, Vitaxin, Vumon, Zanosar, Zinecard, Zofran, Zoladex, Zyloprim, 2 Methoxy-oestradiol.

20. The method according to claim 15 wherein the step of introducing an anti-cancer drug includes incorporating the anti-cancer drug into microbubbles before introduction into the tumor.

21. The method according to claim 15 further comprising the step of introducing microbubbles into the tumor with the anti-cancer drug.

22. A method for inhibiting the sequence of angiogenesis of cancer cells in a tumor, the method comprising the steps of:

transcutaneous introducing an antiangiogenesis agent proximate the cancer cells within the tumor; and introducing ultrasonic energy into the tumor while the antiangiogeneses agent is present therein, the ultrasonic energy being less than 100 kHz at less that 50 watts in order to prevent heating of the tumor.

23. The method according to claim 1 wherein the ultrasonic energy is introduced in a planar non-focused manner.

24. The method according to claim 9 wherein the cancer cells are eradiated with planar non-focused ultrasound.

25. The method according to claim 14 wherein the ultrasonic energy is introduced in a planar non-focused manner.

26. The method according to claim 22 wherein the ultrasonic energy is introduced in a planar non-focused manner.

27. The method according to claim 22 wherein the step of introducing an anti-cancer drug includes incorporating the anti-cancer drug into microbubbles before introduction proximate the cancer cells within the tumor.

28. The method according to claim 22 further comprising the step of introducing microbubbles proximate the cancer cells within the tumor with the anti-cancer drug.

* * * * *